United States Patent
Banerjee et al.

(10) Patent No.: US 11,149,202 B1
(45) Date of Patent: Oct. 19, 2021

(54) TETRACARBOXYLIC ACID COMBINATIONS FOR CORROSION INHIBITION

(71) Applicant: ECOLAB USA, INC., St. Paul, MN (US)

(72) Inventors: Santanu Banerjee, Pune (IN); Anand Harbindu, Pune (IN); Jeffery M. Atkins, Aurora, IL (US); Peter E. Reed, Plainfield, IL (US); Jasbir S. Gill, Naperville, IL (US); Bingzhi Chen, Naperville, IL (US)

(73) Assignee: Ecolab USA Inc., St. Paul, MN (US)

( * ) Notice: Subject to any disclaimer, the term of this patent is extended or adjusted under 35 U.S.C. 154(b) by 794 days.

(21) Appl. No.: 15/838,936

(22) Filed: Dec. 12, 2017

Related U.S. Application Data (60) Provisional application No. 62/433,650, filed on Dec. 13, 2016.

(51) Int. Cl.
| | |
|---|---|
| C09K 15/06 | (2006.01) |
| C07C 55/24 | (2006.01) |
| C09K 15/02 | (2006.01) |
| C09K 15/16 | (2006.01) |
| C23F 11/04 | (2006.01) |
| C08K 5/092 | (2006.01) |

(52) U.S. Cl.
CPC ............. *C09K 15/06* (2013.01); *C07C 55/24* (2013.01); *C08K 5/092* (2013.01); *C09K 15/02* (2013.01); *C09K 15/16* (2013.01); *C23F 11/04* (2013.01); *C08K 2201/019* (2013.01)

(58) Field of Classification Search
CPC ........ C09K 15/06; C09K 15/02; C09K 15/16; C07C 55/24; C08K 5/092; C08K 2201/019; C23F 11/04
USPC ......................................................... 524/321
See application file for complete search history.

(56) References Cited

U.S. PATENT DOCUMENTS

| | | | |
|---|---|---|---|
| 4,046,707 A | 9/1977 | Smith et al. | |
| 4,088,678 A | 5/1978 | Matt et al. | |
| 4,529,756 A | 7/1985 | Salensky | |
| 4,612,049 A | 9/1986 | Berner et al. | |
| 4,696,763 A | 9/1987 | Bentley et al. | |
| 4,719,038 A | 1/1988 | Sobata et al. | |
| 5,000,866 A * | 3/1991 | Woyciesjes | C09K 5/20 252/78.3 |
| 5,018,577 A | 5/1991 | Pardue et al. | |
| 5,023,000 A | 6/1991 | Kneller et al. | |
| 5,085,794 A | 2/1992 | Kneller et al. | |
| 5,137,657 A | 8/1992 | Boffardi | |
| 5,198,482 A | 3/1993 | Phillips et al. | |
| 5,294,371 A | 3/1994 | Clubley et al. | |
| 5,647,995 A | 7/1997 | Kneller et al. | |
| 6,572,789 B1 | 6/2003 | Yang et al. | |
| 6,585,933 B1 * | 7/2003 | Ehrhardt | C23F 11/08 252/180 |
| 7,407,599 B2 | 8/2008 | Turcotte et al. | |
| 7,744,775 B2 | 6/2010 | Yang et al. | |
| 8,207,102 B2 | 6/2012 | Smith | |
| 8,617,415 B2 | 12/2013 | Yang et al. | |
| 8,871,699 B2 | 10/2014 | Silvernail et al. | |
| 9,133,418 B1 | 9/2015 | Miralles | |
| 9,290,851 B2 | 3/2016 | Gill et al. | |
| 9,359,678 B2 | 6/2016 | Garner | |
| 9,534,300 B2 | 1/2017 | Gill et al. | |
| 2007/0120094 A1 * | 5/2007 | Yang | C23F 11/08 252/389.2 |
| 2008/0169243 A1 | 7/2008 | Dave et al. | |
| 2011/0253628 A1 | 10/2011 | Blokker et al. | |
| 2014/0131283 A1 | 5/2014 | Relenyi et al. | |
| 2014/0228275 A1 | 8/2014 | Olson et al. | |
| 2014/0235521 A1 | 8/2014 | Silvernail et al. | |
| 2014/0238445 A1 | 8/2014 | Stokes et al. | |
| 2014/0251502 A1 | 9/2014 | Wei et al. | |
| 2014/0261564 A1 | 9/2014 | Miralles | |
| 2014/0261567 A1 | 9/2014 | Miralles | |
| 2014/0309340 A1 | 10/2014 | Schneider et al. | |
| 2014/0378366 A1 | 12/2014 | Silvernail et al. | |
| 2015/0004054 A1 | 1/2015 | Richardson et al. | |

(Continued)

FOREIGN PATENT DOCUMENTS

| | | |
|---|---|---|
| CA | 1316685 | 4/1993 |
| CN | 101289256 A | 10/2008 |

(Continued)

OTHER PUBLICATIONS

Blanchard, Eugene J. et al., "Improved Flame Resistance of Cotton/Polyester Fleece with Phosphorus-Based Polycarboxylic" American Association of Textile Chemists & Colorist Feb. 26-30, 2005, www.AATCC.org.

Demadis, Konstantinos D. et al., "Phosphonopolycarboxylates as Chemical Additives for Calcite Scale Dissolution and Metallic Corrosion Inhibition Based on a Calcium-Phosphonotricarboxylate Organic-Inorganic Hybrid" Crystal Growth & Design (2006) 6(5): 1064-1067.

Pudovik, A.N. et al., "New Method of Synthesis of Esters of Phosphonic and Thio-phosphonic Acids" Zhurnal Obshchei Khimii (1959) 29: 3338-42.

(Continued)

*Primary Examiner* — Ling Siu Choi
*Assistant Examiner* — Ronald Grinsted
(74) *Attorney, Agent, or Firm* — Eric D. Babych; Barnes & Thornburg LLP (57) ABSTRACT

Corrosion inhibitors and methods for reducing or inhibiting corrosion of metals in aqueous systems are provided. Corrosion inhibitor compositions may include tetracarboxylic acids, such as butane tetracarboxylic acid. The compositions may include other components, such as zinc, molybdate, silicate, cerium, among others. The compositions may also include polymers or oligomers. The corrosion inhibitor compositions produced synergistic results and unexpectedly low corrosion rates.

18 Claims, 4 Drawing Sheets

(56) References Cited

U.S. PATENT DOCUMENTS

| | | |
|---|---|---|
| 2015/0354067 A1 | 12/2015 | Gill et al. |
| 2016/0010035 A1 | 1/2016 | Liu et al. |
| 2016/0017200 A1 | 1/2016 | Yang et al. |
| 2016/0083562 A1 | 3/2016 | Ye et al. |
| 2016/0158960 A1 | 6/2016 | Matsumura |
| 2016/0281020 A1 | 9/2016 | Yamamoto et al. |
| 2016/0348252 A1 | 12/2016 | Rane et al. |
| 2016/0348253 A1 | 12/2016 | Harbindu et al. |
| 2017/0027065 A1 | 1/2017 | Wei et al. |

FOREIGN PATENT DOCUMENTS

| | | |
|---|---|---|
| CN | 102181023 A | 9/2011 |
| CN | 102745823 A | 10/2012 |
| CN | 103820785 A | 5/2014 |
| CN | 104724838 A | 6/2015 |
| EP | 0183647 B1 | 2/1989 |
| EP | 0454323 A1 | 10/1991 |
| EP | 0375614 B1 | 3/1993 |
| EP | 0564346 A1 | 10/1993 |
| EP | 0786018 B1 | 1/2002 |
| JP | 2000309594 A | 11/2000 |
| JP | 2000309612 A | 11/2000 |
| JP | 2013204148 | 10/2013 |
| JP | 2017025046 | 2/2017 |
| SU | 376388 | 4/1973 |
| WO | WO 2000/005434 A1 | 2/2000 |
| WO | WO 0066810 | 11/2000 |
| WO | WO 02079105 A1 | 10/2002 |
| WO | WO 03033806 | 4/2003 |
| WO | WO 03033807 | 4/2003 |
| WO | WO 03033811 A1 | 4/2003 |
| WO | WO 03033812 A1 | 4/2003 |
| WO | WO 2009055377 | 4/2009 |
| WO | WO 2009074664 A1 | 6/2009 |
| WO | WO 2009074667 A1 | 6/2009 |
| WO | WO 2014042931 A1 | 3/2014 |

OTHER PUBLICATIONS

Prishchenko, Andrey A. et al., "Synthesis of New Organophosphorus-Substituted Derivatives of Functionalized Propionates and Their Analogues" Heteroatom Chemistry (2008) 19(4): 418-428.

Xiang, Lijun et al., "Research on the properties of controlling corrosion and scale inhibition of the modified starch with microwave loading" (2014) 997: 9-15.

RN 5702-98-7 Registry Nov. 16, 1984.

RN 136266-82-5 Registry Sep. 20, 1991.

RN 514847-68-8 Registry May 14, 2003.

RN 774534-67-7 Registry Nov. 4, 2004.

RN 1143570-77-7 Registry May 7, 2009.

RN 1572424-95-3 Registry Mar. 24, 2014.

RN 1630990-17-8 Registry Oct. 30, 2014.

Liu, Xiao Shan, et al. "Study on novel eco-friendly anti-creasing agents for natural silk fabric," Chinese Chemical Letters (2012) 23: 665-668.

Mayer, Bernd et al. "Environmentally Sound Corrosion Inhibitors for Cooling Water," Henkel Technologies, Water Treatment (2002) TL6: 1-16, www.henkel-water.com.

Ochoa, N., et al. "The synergistic effect between phosphonocarboxylic acid salts and fatty amines for the corrosion protection of a carbon steel," Journal of Applied Electrochemistry (2004) 34: 487-493.

Orhan, Mehmet, et al. "Improving the Antibacterial Activity of Cotton Fabrics Finished with Triclosan by the Use of 1,2,3,4-Butanetetracarboxylic Acid and Citric Acid," Journal of Applied Polymer Science (2008) III(3): 1344-1352.

* cited by examiner

TETRACARBOXYLIC ACID COMBINATIONS FOR CORROSION INHIBITION

BACKGROUND

1. Field of the Invention

The present disclosure generally relates to corrosion control. More particularly, the disclosure pertains to corrosion inhibitor compositions containing tetracarboxylic acid compounds and methods of reducing or inhibiting corrosion of metallic surfaces in aqueous systems.

2. Description of the Related Art

Carbon steel corrosion inhibition has evolved over many decades from the use of chromate to the current heavy metals and phosphate chemistries. Several decades ago, chromate was banned and was predominantly replaced by molybdenum, zinc, silicate and phosphate. Several advances have been made in the phosphate chemistries from the use of orthophosphate to polyphosphate and the use of organic phosphates, phosphonates, and phosphinates. Currently, phosphorus is under environmental pressure and may only be used in very low-level quantities.

Ferrous metals, such as carbon steel, are among the most commonly used structural materials in industrial systems. Loss of the metals from surfaces resulting from general corrosion causes deterioration of the structural integrity of the system or structure because of reduction of mechanical strength. Localized corrosion (e.g. pitting) may pose an even greater threat to the normal operation of the system than general corrosion because such corrosion will occur intensely in one particular location and may cause perforations in the system structure carrying an industrial water stream. These perforations may cause leaks which require shutdown of the entire industrial system so that repair can be made. Indeed, corrosion problems usually result in immense maintenance costs, as well as costs incurred as a result of equipment failure. Therefore, the inhibition of metal corrosion in industrial water is critical.

Corrosion protection of ferrous metals in industrial water systems is often achieved by adding a corrosion inhibitor. Many corrosion inhibitors, including chromate, molybdate, zinc, nitrite, orthophosphate, and polyphosphate have been used previously, alone or in combination, in various chemical treatment formulations. However, these inorganic chemicals can be toxic, detrimental to the environment, and/or not very effective against localized corrosion, especially at economically feasible and/or environmentally acceptable low dosage levels.

Corrosion has also been managed by using more corrosion resistant materials, applying protective coatings, and/or using sacrificial anode or chemical treatment. Since aqueous corrosion has been shown to consist of, for most part, an electrochemical process, the chemical treatments have been applied as anodic inhibitors, cathodic inhibitors, or a combination of cathodic and anodic inhibitors.

BRIEF SUMMARY

The present disclosure generally relates to corrosion inhibitor compositions. An embodiment of the present disclosure relates to a corrosion inhibitor composition, which may include a tetracarboxylic acid compound of formula (I)

where $R_1$, $R_3$, $R_4$, and $R_5$ may each be a $C_1$-$C_6$ alkylene group. The variable $R_2$ may be CH or CHR', where R' may be a $C_1$-$C_6$ alkylene group. In some embodiments tetracarboxylic acid compound of formula (I) is not 1,2,3,4-butane tetracarboxylic acid.

In other embodiments, the disclosure relates to a corrosion inhibitor composition, which may include a tetracarboxylic acid compound selected from $C_3$-$C_{12}$ alkyl tetracarboxylic acid, $C_3$-$C_{12}$ aryl tetracarboxylic acid, $C_3$-$C_{12}$ cycloalkyl tetra carboxylic acid, aspartic acid N,N bis(carboxymethyl)-3-hydroxy, any salt thereof, or any combination thereof.

In some embodiments, the disclosures relates to a corrosion inhibitor composition, which may include a tetracarboxylic acid compound, an additional corrosion inhibitor selected from zinc, tin, aluminum, manganese, nickel, silicate, molybdate, strontium, titanium, chromate, cobalt, cerium, any salt thereof, any oxide thereof, or any combination thereof. A polymer may be added that includes one or more monomers selected from acrylic acid, 2-acrylamido-2-methylpropane sulfonic acid, itaconic acid, tertiary butyl acrylamide, acrylamide, methacrylamide, or any combination thereof.

In other embodiments, the disclosure relates to a method of inhibiting corrosion of a metallic surface in an aqueous system, which may include adding a corrosion inhibitor composition to the aqueous system. The corrosion inhibitor composition may include a tetracarboxylic acid compound and an additional corrosion inhibitor selected from zinc, tin, aluminum, manganese, nickel, silicate, molybdate, strontium, titanium, chromate, cobalt, cerium, any salt thereof, any oxide thereof, or any combination thereof.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

BRIEF DESCRIPTION OF THE SEVERAL VIEWS OF THE DRAWINGS

A detailed description of the invention is hereafter described with specific reference being made to the drawings in which.

DETAILED DESCRIPTION

Various embodiments are described below. The relationship and functioning of the various elements of the embodiments may better be understood by reference to the following detailed description. However, embodiments are not limited to those illustrated below. In certain instances details may have been omitted that are not necessary for an understanding of embodiments disclosed herein.

The present disclosure relates to corrosion inhibitor compositions and methods for inhibiting corrosion. The corrosion inhibitor compositions include tetracarboxylic acid compounds. The corrosion inhibitor compositions can effectively reduce, inhibit, and/or prevent corrosion in soft or hard water on surfaces comprising metals. In some aspects, the metals are ferrous metals, such as steel, iron, and alloys of iron with other metals, such as stainless steel.

The presently disclosed corrosion inhibitor compositions show strong efficacy as corrosion inhibitors for surfaces comprising carbon steel metallurgy, ferrous metals, and the like. The corrosion inhibitor compositions can achieve a high level of corrosion inhibition without the use of chemistries containing phosphorus and such high levels of corrosion inhibition, such as less than 3 mpy, may also be achieved when using only a small amount of the presently disclosed corrosion inhibitor compositions. The combination of tetracarboxylic acids with other additives produced synergistic results with unexpectedly high levels of corrosion inhibition.

In some embodiments, a composition for preventing corrosion may comprise a tetracarboxylic acid compound of formula (I), shown below.

(I)

The variables $R_1$, $R_3$, $R_4$, and $R_5$ may be each independently a $C_1$-$C_6$ alkylene group. An alkylene group is a bivalent saturated aliphatic radical. The alkylene group may be substituted with hydrogen, $C_1$-$C_6$ alkyl, or COOH. The variable $R_2$ may be CH or CHR', where R' is a $C_1$-$C_6$ alkylene group. In other embodiments, the tetracarboxylic acid compounds encompassed by formula (I) do not include 1,2,3,4-butane tetracarboxylic acid.

In some embodiments, $R_1$, $R_3$, $R_4$, $R_5$, and R' may be substituted independently with a hydrogen, $C_1$-$C_6$ alkyl, COOH, $C_4$ to $C_6$ aryl, $C_1$ to $C_{10}$ alkoxy, hydroxyl, cumene, mesitylene, toluene, or xylene. In certain embodiments, the tetracarboxylic acid compounds in the present disclosure may include more than four carboxylic acid functional groups. The compounds may comprise 5, 6, 7, 8, or 9 carboxylic acid functional groups covalently attached to the compound, for example.

In some embodiments, a corrosion inhibitor composition may comprise one or more tetracarboxylic acid compounds such as a $C_3$-$C_{12}$ alkyl tetracarboxylic acid, $C_3$-$C_{12}$ aryl tetracarboxylic acid, $C_3$-$C_{12}$ cycloalkyl tetracarboxylic acid, or Aspartic acid N, N bis(carboxymethyl)-3-hydroxy. In particular embodiments, the compounds may be in the form of a salt. The carboxylic acid groups may be bound to separate carbon atoms or to the same carbon atom, for example propane tetracarboxylic acid may be 1,1,2,3-propane tetracarboxylic acid.

In certain embodiments, any of the corrosion inhibitor compositions in the present disclosure may comprise one or more additional corrosion inhibitors such as, but not limited to, zinc, tin, aluminum, manganese, nickel, silicate, molybdate, strontium, titanium, chromate, cobalt, or cerium. The additional corrosion inhibitors may be in the form of any salt or any oxide. Illustrative, non-limiting examples of inorganic salts may be chloride, nitrate, nitrite, or sulfate. The salt form may be organic including, but not limited to, acetate or citrate salts.

In certain embodiments, a corrosion inhibitor composition comprises an effective amount of the tetracarboxylic acid compound and an additional corrosion inhibitor. In some embodiments, the weight ratio of tetracarboxylic acid compound to additional corrosion inhibitor is about 10:1. In some embodiments, the weight ratio is about 1:1, about 2:1, about 3:1, about 4:1, or about 5:1. In some embodiments, the amount of corrosion inhibitor in the aqueous system after the composition has been added may range from about 0.1 ppm to about 50 ppm. In other embodiments, the amount of corrosion inhibitor may range from about 0.5 ppm to about 5 ppm, about 1 ppm to about 4 ppm, or about 1 ppm to about 3 ppm. In other embodiments, the amount of corrosion inhibitor may range from about 5 ppm to about 30 ppm, about 10 ppm to about 20 ppm, or about 5 ppm to about 20 ppm.

In some embodiments, the tetracarboxylic acid compound may be one or more of BTCA, 1,1,2,3-propane tetracarboxylic acid, 1,2,4,5-benzene tetracarboxylic acid, 1,2,3,4-cyclopentane tetracarboxylic acid, Aspartic acid N,N bis(carboxymethyl)-3-hydroxy, cycloalkane tetracarboxylic acid, and/or any salt thereof.

In other embodiments, the alkyl tetracarboxylic acid compound may be pentane tetracarboxylic acid, hexane tetracarboxylic acid, heptane tetracarboxylic acid, octane tetracarboxylic acid, nonane tetracarboxylic acid, decane tetracarboxylic acid, undecane tetracarboxylic acid, dodecane tetracarboxylic acid or any salt thereof.

In some embodiments, the cycloalkyl tetracarboxylic acid may be cyclopropane tetracarboxylic acid, cyclobutane tetracarboxylic acid, cyclopentane tetracarboxylic acid, cyclohexane tetracarboxylic acid, or cyclooctane tetracarboxylic acid. The tetracarboxylic acid compound may be 1,3,5,7-adamantanetetracarboxylic acid.

In some embodiments, the tetracarboxylic acid compound may be BTCA or any salt thereof, and the additional corrosion inhibitor is zinc or any salt thereof. In another embodiment, the tetracarboxylic acid compound may be BTCA or any salt thereof, and the additional corrosion inhibitor may be molybdate or any salt thereof. In another embodiment, the tetracarboxylic acid compound may be BTCA or any salt thereof, and the additional corrosion inhibitor may be silicate or any salt thereof. In some embodiments, the tetracarboxylic acid compound may be BTCA or any salt thereof and the additional corrosion inhibitor may be tin or any salt thereof.

In certain embodiments, any of the compositions in this disclosure may include a polymer comprising one or more monomers of acrylic acid, 2-acrylamido-2-methylpropane sulfonic acid (AMPS), itaconic acid, tertiary butyl acrylamide, acrylamide, methacrylamide, and any combination thereof. The polymer may be a homopolymer, copolymer, terpolymer or tetrapolymer comprising varying proportions of monomers not limited to those listed above. In certain embodiments, the polymer may comprise about 80 to about 99 mole percent acrylic acid and from about 1 to about 20 mole percent AMPS. In some embodiments, the copolymer may comprise about 95% acrylic acid and about 4% AMPS or about 90% acrylic acid and about 10% AMPS. In other embodiments, the polymer may be a tetrapolymer comprising acrylic acid, itaconic acid, AMPS, and tertiary butyl acrylamide in any mole percent. Other polymers that may be used in the corrosion inhibitor compositions include, but are not limited to, copolymers of acrylic acid and AMPS comprising about 40 to about 70% acrylic acid and about 30 to about 60% AMPS. In other embodiments, the polymer may be a copolymer comprising about 60% acrylic acid and about 40% AMPS or about 50% acrylic acid and about 50% AMPS.

In certain embodiments, the composition comprises an effective amount of polymer, which may be appropriately selected by one of skill in the art. The amount of polymer in the aqueous system after the composition has been added may range from about 0.1 ppm to about 100 ppm. In other embodiments, the amount of polymer may range from about 1 ppm to about 50 ppm, about 1 ppm to about 10 ppm, or about 1 ppm to about 20 ppm. In other embodiments, the amount of polymer may range from about 5 ppm to about 30 ppm, about 10 ppm to about 20 ppm, or about 5 ppm to about 20 ppm.

In some embodiments, any of the compositions of the present disclosure may comprise an oligomeric maleic acid or oligomeric maleic anhydride (OMA) of formula (II) or formula (III) shown below.

The variable "n" may be 1, 2, 3, 4, 5, or 6. Additionally, OMA may be substituted at the $R_6$ and $R_7$ position in formula (II) or formula (III) with a suitable substituent. Suitable substituents may include hydrogen, $C_1$-$C_{10}$ alkyl, $C_4$ to $C_6$ aryl, $C_1$ to $C_{10}$ alkoxy, or hydroxyl. Substituents may also include cumene, mesitylene, toluene, or xylene. OMA may be synthesized in organic solvents such as, cumene, mesitylene, toluene, xylene, etc., or in water. Appropriate catalysts and reaction conditions may be used as needed.

In some embodiments, the OMA compound may have any one of the following structures:

In certain embodiments, the corrosion inhibitor composition comprises an effective amount of OMA, which may be appropriately selected by one of skill in the art. The amount of OMA in the aqueous system after the composition has been added may range from about 0.1 ppm to about 100 ppm. In other embodiments, the amount of OMA may range from about 1 ppm to about 50 ppm, about 1 ppm to about 10 ppm, or about 1 ppm to about 20 ppm. In other embodiments, the amount of OMA may range from about 10 ppm to about 50 ppm, about 10 ppm to about 40 ppm, or about 20 ppm to about 50 ppm.

In some embodiments, the corrosion inhibitor composition may include a byproduct and/or a reactant from the chemical synthesis of BTCA. The synthesis of BTCA may produce byproducts, some of which may be intermediates. An intermediate in the chemical synthesis is tetrahydrophthalic acid (THPA). Reagents used in BTCA synthesis that may be present in the reaction mixture include 3a,4,7,7a-tetrahydroisobenzofuran-1,3-dione, hydrogen peroxide, and/or sodium tungstate. In certain embodiments, the corrosion inhibitor composition may comprise the crude or unpurified reaction mixture of the synthesis of BTCA. The crude or unpurified reaction mixture may contain chemical byproducts including, but not limited to, THPA and 4,5-dihydroxycyclohexane-1,2-dicarboxylic acid (DHCHDA). The unpurified reaction mixture may comprise about 10 to about 40% by weight BTCA, and the amount of THPA in the reaction mixture may be less than or equal to about 1% by weight. The amount of DHCHDA in the reaction mixture may range from about 0 to about 20 mole %. In some embodiments, the amount of DHCHDA ranges from about 5 to about 15 mole %.

In other embodiments, any of the compositions may include an effective amount of tetracarboxylic acid, which may comprise from about 5% to about 50% by weight of the tetracarboxylic acid compound. In other embodiments, the composition may comprise from about 0.5% to about 15% by weight of the additional corrosion inhibitor. The effective amount is not limited and may be appropriately selected by one of ordinary skill in the art depending upon the particular aqueous system, the water chemistry, etc. In some aspects, the effective amount in the aqueous system is from about 2 ppm to about 200 ppm. In other aspects, the effective amount is from about 5 to about 100 ppm. In still other aspects, the effective amount is less than about 35 ppm. In one particular aspect, the effective amount is about 10 ppm to about 50 ppm.

In one embodiment, a corrosion inhibitor composition comprises a tetracarboxylic acid compound, an additional corrosion inhibitor selected from the group consisting of zinc, tin, aluminum, manganese, nickel, silicate, molybdate, strontium, titanium, chromate, cobalt, cerium, any salt thereof, any oxide thereof, and any combination thereof, and a polymer. The additional corrosion inhibitor may be one or more of zinc, tin, aluminum, manganese, nickel, silicate, molybdate, strontium, titanium, chromate, cobalt, cerium, any salt thereof, or any oxide thereof. The polymer may comprise one or more monomers of acrylic acid, AMPS, itaconic acid, tertiary butyl acrylamide, acrylamide, or methacrylamide.

In some embodiments, the composition may comprise OMA of formula (II) or formula (III) in addition to a tetracarboxylic acid compound, an additional corrosion inhibitor, and a polymer. In certain embodiments, the additional corrosion inhibitor may be zinc or any salt thereof. In other embodiments, the additional corrosion inhibitor may be tin or any salt thereof.

In some embodiments, any of the compositions in the present disclosure may comprise a triazole. Illustrative triazoles include, but are not limited to, toly triazole, benzo triazole, and butyl benzo triazole.

In some embodiments, any composition of the present disclosure may exclude phosphorus, phosphorus-containing corrosion inhibitors, and/or tetrazolium compounds.

The present disclosure also includes methods of using the compositions disclosed herein to prevent, reduce, and/or inhibit corrosion. It is to be understood that when referring to methods of inhibiting corrosion, methods of preventing and/or reducing corrosion are also included. In some embodiments, a method of inhibiting corrosion of a metallic surface in an aqueous system includes adding a corrosion inhibitor composition to the aqueous system. The corrosion inhibitor composition comprises a tetracarboxylic acid compound and an additional corrosion inhibitor. The additional corrosion inhibitor may be one or more of zinc, tin, aluminum, manganese, nickel, silicate, molybdate, strontium, titanium, chromate, cobalt, cerium, any salt thereof, or any oxide thereof.

In some embodiments, the tetracarboxylic acid compound may be BTCA or any salt thereof and the additional corrosion inhibitor may be zinc or any salt thereof. In other embodiments, the metallic surface in the aqueous system comprises iron or any iron oxide.

In some embodiments, a method of inhibiting corrosion may comprise adding the components of the corrosion inhibitor composition separately to the aqueous system, adding certain components separately and certain components together to the aqueous system, or adding all components of the composition together. The compositions (or components thereof) may be dosed periodically or continuously into the aqueous system.

The presently disclosed corrosion inhibitor compositions may be used in any aqueous system comprising surfaces susceptible of corrosion. For example, the corrosion inhibitor compositions may be used in once-through, open loop, or closed loop recirculating cooling water systems. Other aqueous systems include, but are not limited to, systems used in petroleum production and oil recovery (e.g., well casing transport pipelines, etc.) and refining, geothermal wells, and other oil field applications; boilers and boiler water systems; systems used in power generation, mineral process waters including mineral washing, flotation and benefaction; paper mill digesters, washers, bleach plants, white water systems and mill water systems; black liquor evaporators in the pulp industry; gas scrubbers and air washers; continuous casting processes in the metallurgical industry; air conditioning and refrigeration systems; building fire protection heating water, such as pasteurization water; water reclamation and purification systems; membrane filtration water systems; food processing streams and waste treatment systems as well as in clarifiers, liquid-solid applications, municipal sewage treatment systems; and industrial or municipal water distribution systems.

In particular aspects of the present disclosure, the corrosion inhibitor compositions may be used in connection with warewashing compositions. Warewashing compositions may be used for protecting articles, such as glassware or silverware, from corrosion in a dishwashing or warewashing machine. However, it is to be understood that the warewashing compositions comprising the presently disclosed corrosion inhibitor compositions can be available for cleaning environments other than inside a dishwashing or warewashing machine.

The corrosion inhibitor composition may be included in the warewashing composition in an amount sufficient to provide a use solution that exhibits a rate of corrosion and/or etching of glass that is less than the rate of corrosion and/or etching of glass for an otherwise identical use solution, except for the absence of the corrosion inhibitor composition.

In some embodiments, the corrosions inhibitor compositions may comprise, consist of, or consist essentially of any of the features listed in in the disclosure herein.

In certain embodiments, the disclosed corrosion inhibitor compositions may comprise one or more of the following characteristics:

Halogen stability up to about 0.5 ppm free residual chlorine (FRC);
Ability to handle water temperatures up to about 60° C.;
Compatibility with azoles, dispersants, and cooling water polymers;
Calcium tolerance up to 500 ppm as $CaCO_3$;
Chloride tolerance up to 600 ppm as Cl;
Stability over a pH from about 6 to about 9;
Low toxicity (e.g. LC50>100 mg/L); and
Stable for a Holding Time Index (HTI) of from a few seconds up to about 240 hours.

EXAMPLES

Example 1: Synthesis of BTCA

A synthesis according to Scheme 1 was performed. A 250 ml round-bottomed flask equipped with a magnetic stirring bar and a reflux condenser was charged with 0.2167 g (0.0657 mmol) of sodium tungstate ($Na_2WO_4$). Water and 32.8 g (0.289 mol) of aqueous 30% hydrogen peroxide ($H_2O_2$) was added. The mixture was vigorously stirred at room temperature for 10 min and then 10 g (0.0657 mol) of 3a,4,7,7a-tetrahydroisobenzofuran-1,3-dione (Compound 1) was added. The mole ratio of Compound 1:$H_2O_2$:$Na_2WO_4$ was 1:4.4:0.01. The biphasic mixture was heated successively at 75° C. for 30 min, at 80° C. for 30 min, at 85° C.

for 30 min, and at 90° C. for 6.5 hours, with vigorous stirring. The homogeneous solution was cooled down and collected for analysis.

Scheme 1

After the reaction the content of BTCA was measured in the reaction mixture using high pressure liquid chromatography (HPLC). The weight percent of BTCA was 24% and the byproduct tetrahydrophthalic acid (THPA is Compound 2 in Scheme 1) was not detected.

Example 2: Synthesis of BTCA

A 250 ml round-bottomed flask equipped with a magnetic stirring bar, a reflux condenser and connected with paraffin oil trap was charged with 0.432 g of $Na_2WO_4$, water, and 65 g of aqueous 30% $H_2O_2$. The mixture was vigorously stirred at room temperature for 10 min and then 20 g of Compound 1 was added. The mole ratio of Compound 1:$H_2O_2$:$Na_2WO_4$ was 1:4.4:0.01. The biphasic mixture was heated up to 90° C., a high exotherm was observed at ~50° C. with high oxygen evolution, which ceased after a few seconds. The homogeneous solution was cooled down and collected for analysis.

After completing the steps above, samples were taken of the reaction mixture to determine the content of BTCA and THPA using HPLC. The weight percent of BTCA in the reaction mixture was 33.1% and the weight percent of THPA was less than 1%.

Example 3: Synthesis of BTCA

A 250 ml round-bottomed flask equipped with a magnetic stirring bar, a reflux condenser, and connected with paraffin oil trap was charged with 0.432 g of $Na_2WO_4$, water, and 65 g of aqueous 30% $H_2O_2$. The mixture was vigorously stirred at room temperature for 10 min and then 20 g of Compound 1 was added. The biphasic mixture was heated. A high exotherm was observed at ~50° C. with high oxygen evolution, which ceased in few seconds then reaction mixture again heated for 8 hours at 90° C. The homogeneous solution was cooled down and collected for analysis.

An NMR sample was prepared by dissolving the powder in D2O. Quantitative proton spectra were used to quantize the mole % of each component. Total Correlation (TOCSY) and Heteronuclear single quantum coherence (HSQC) spectra were acquired to characterize the structures of major components. The stacked proton spectra of BTCA at 5.5 hr and 8 hr appeared almost identical. The TOCSY spectrum of sample at 5.5 hr suggested there are two major spin systems (i.e. two major components). The carbon chemical shifts from HSQC spectrum suggested the presence of hydroxylated carbon in the minor species. All NMR results indicate the major component was BTCA and the second major component was the unreacted 4,5-dihydroxycyclohexane-1,2-dicarboxylic acid (DHCHDA). The quantitative analysis indicated that the desired BTCA in the sample at 5.5 hr was about 91 mole % and the unreacted DHCHDA was about 9 mole %. The BTCA in sample at 8 hr dropped slightly to about 89 mole % and the unreacted DHCHDA was about 11 mole %. Although we can detect some trace components, they consist of much less than 1 mole % and are challenging for to characterize using NMR.

Example 4: Standard Electrochemical Corrosion Test Protocol

Electrochemical Gamry technique is used for measuring corrosion inhibition performance of new polymers as corrosion inhibitors. The test is performed using three different types of water matrices: soft, medium soft and high hardness/chloride water. The water chemistry is prepared by adding required amount of mineral salts (as source for different metal cations and anions) in deionized water.

The composition in water is given below:
Ca (as calcium carbonate)=220 mg/L
Mg (as calcium carbonate)=100 mg/L
$HCO_3$ (as calcium carbonate)=100 mg/L
Chloride as Cl=70 mg/L
Sulfate as $SO_4$=300 mg/L
Sodium as Na=80 mg/L A volume of 800 ml of water was used in a 1 L round bottom glass flask that was heated using a temperature controller to 120° F., and the solution was simultaneously purged with air (very low rate). The study was done in a well aerated system, and the pH was maintained at 8.0-8.2 with CO2, throughout the study. Components (tetracarboxylic acid, corrosion inhibitor, polymer, OMA etc.) of the corrosion inhibitor compositions were dosed at 1-50 ppm as active chemical in the test cell.

The Gamry electrochemical instrument operates through a rotary electrode principle and contains a Rotating Cylinder Electrode, for which the rotator speed should be set at 500 rpm. The experiment continued for 48 hours duration. The corrosion rate was measure periodically over the 48 hours. After 24 hours an oxidizing biocide (bleach) was dosed for the remaining 24 hours.

Gamry software collected the data through polarization resistance measurements at a potential scan rate of 0.1 mV/second within 20 mV of the corrosion potential from the cathodic region to the anodic region. A corrosion rate (mpy) versus time curve was plotted using the Gamry software and the steady state corrosion rate was determined with this plot.

Example 5: Steady State Corrosion Rates for Various Compositions

Figure 1:
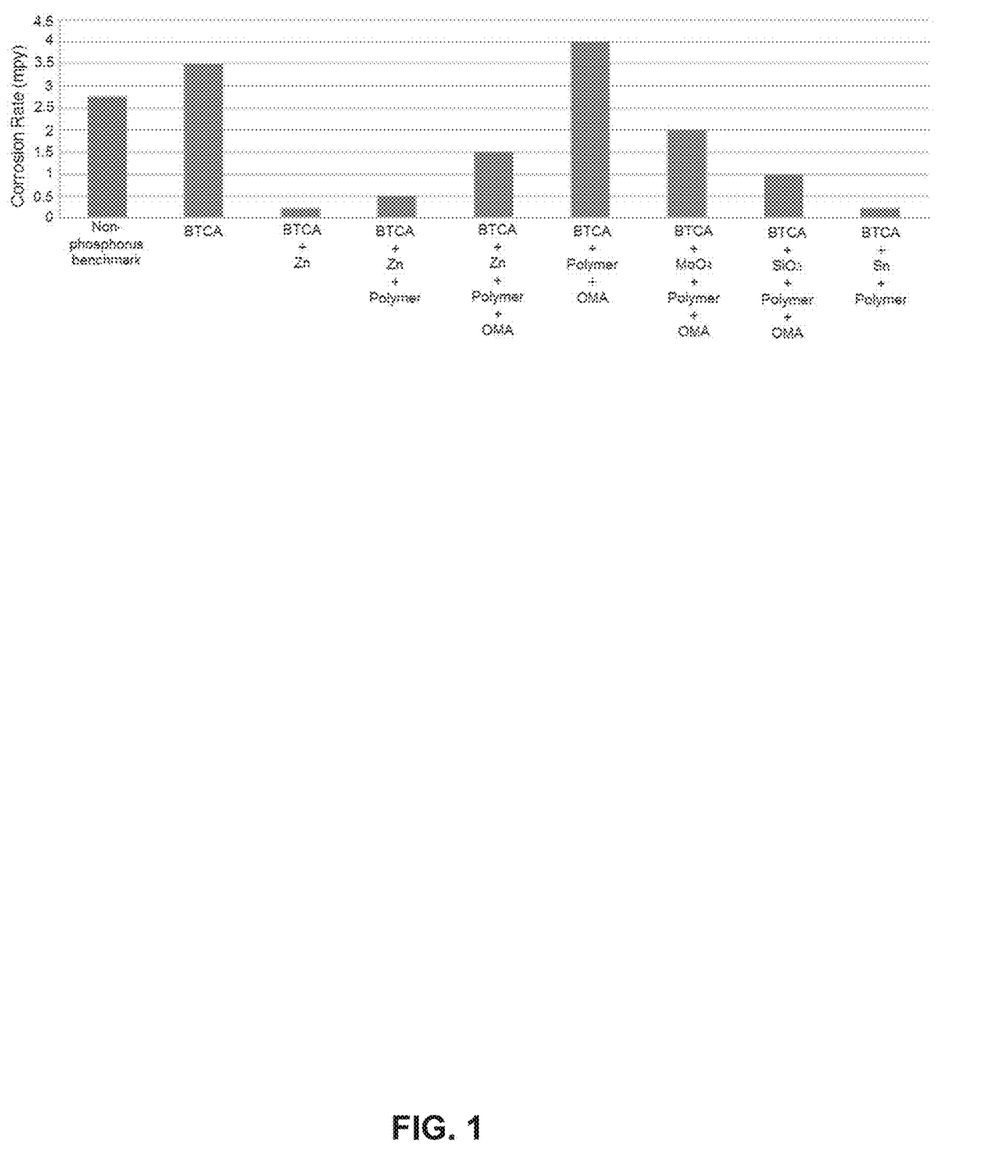
FIG. 1 shows corrosion rates for compositions containing 1,2,3,4-butane tetracarboxylic acid (BTCA)

The steady state corrosion rates of the compositions in the present disclosure were compared to a non-phosphorus benchmark compound. The compositions showed synergism in certain combinations resulting in unexpectedly low corrosion rates. FIG. 1 shows the corrosion rate in mils penetration per year (mpy) for various compositions. Unexpectedly, a composition containing BTCA and Zn resulted in a surprisingly low corrosion rate of less than 0.5 mpy. The tetracarboxylic acid BTCA produced lower corrosion rates than BCTA alone or non-phosphorus benchmark when BTCA was combined with other components such as molybdate ($MoO_4$), $SiO_3$, and Sn. The combination of BTCA, Sn, and polymer (tetrapolymer comprising acrylic acid, itaconic acid, AMPS, and tertiary butyl acrylamide) slowed corrosion to an unexpectedly low rate of around 0.25 mpy. The polymer used in the compositions was a copolymer of acrylic acid and AMPS (60:40) unless specified otherwise.

Example 6: Corrosion Inhibition in Soft Water

Figure 2:
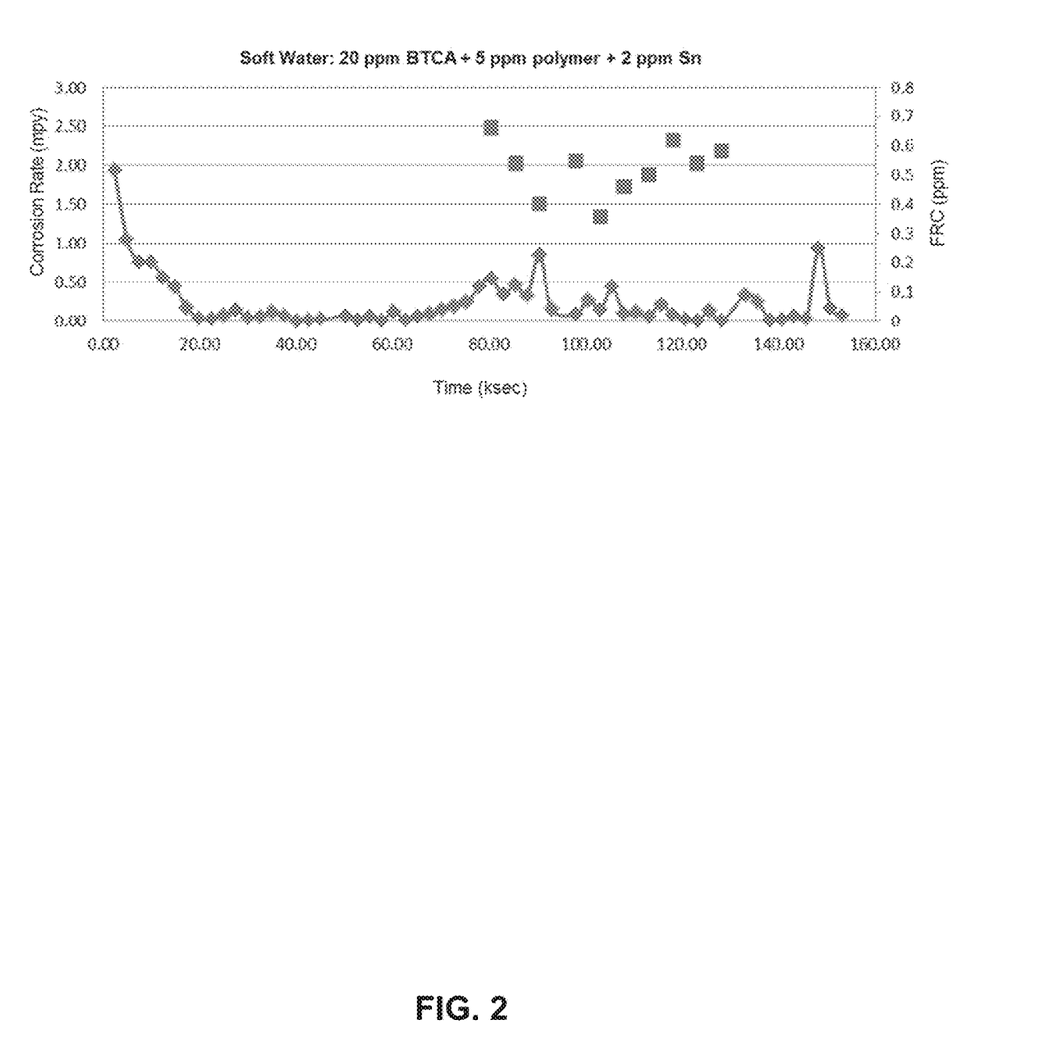
FIG. 2 shows the change in corrosion rate over time in soft water comprising 20 ppm BTCA, 5 ppm polymer, and 2 ppm Sn.

The compositions of the present disclosure show effective inhibition of corrosion in soft water. FIG. 2 shows the corrosion rate (mpy) over time in water comprising 20 ppm BTCA, 5 ppm polymer (tetrapolymer comprising acrylic acid, itaconic acid, AMPS, and tertiary butyl acrylamide), and 2 ppm Sn (tin). The corrosion rate dropped to below 0.5 mpy in about 5 hours.

Example 7: Synergism of BTCA and Zn

Figure 3:
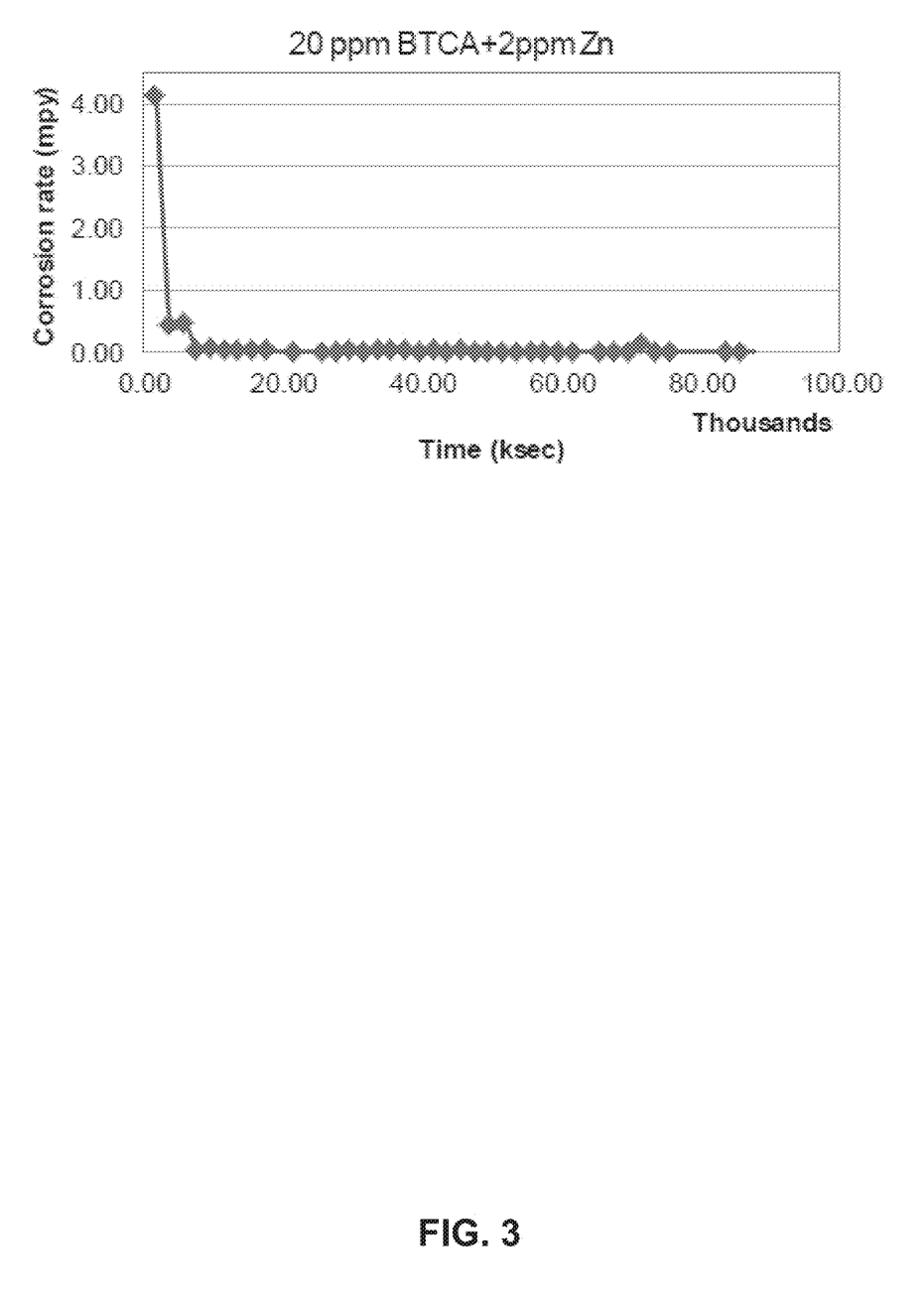
FIG. 3 shows the change in corrosion rate over time in water comprising 20 ppm BTCA and 2 ppm Zn.

The corrosion rate dropped rapidly when BTCA and Zn were present in the water in amounts of 20 ppm and 2 ppm, respectively (See FIG. 3). The corrosion rate dropped by approximately 14 times when Zn was combined with BTCA.

Example 8: Synergism of BTCA, Zn, and Polymer (Copolymer of Acrylic Acid and AMPS (60:40

Figure 4:
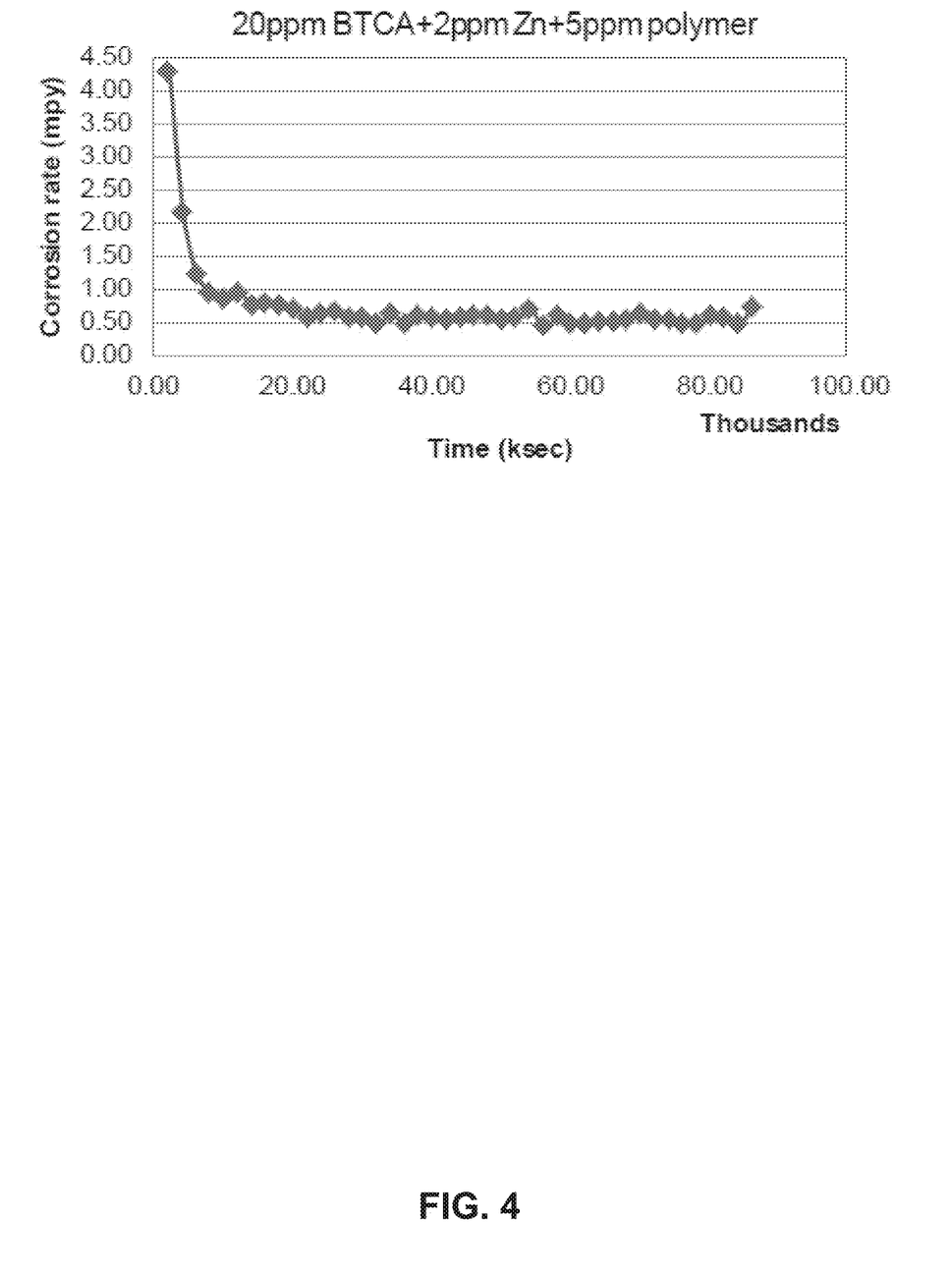
FIG. 4 shows the change in corrosion rate over time in water comprising 20 ppm BTCA, 2 ppm Zn, and 5 ppm polymer.

FIG. 4 shows that the corrosion rate reached a steady state below 1 mpy at about 0.5 mpy. Additionally, the corrosion rate shown in FIG. 4 and for other compositions decreased rapidly demonstrating a significant improvement over other non-phosphorus corrosion inhibitor compositions.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a polymer" is intended to include "at least one polymer" or "one or more polymers."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A corrosion inhibitor composition, comprising:
a tetracarboxylic acid compound of formula (I)

where $R_1$, $R_3$, $R_4$, and $R_5$ are each independently selected from a group consisting of $C_1$-$C_6$ alkylene, $C_1$-$C_6$ alkyl, $C_4$ to $C_6$ aryl, $C_1$ to $C_{10}$ alkoxy, cumene, mesitylene, toluene, and xylene;

$R_2$ is CH or CHR', where R' is a selected from a group consisting of $C_1$-$C_6$ alkylene, $C_1$-$C_6$ alkyl, $C_4$ to $C_6$ aryl, $C_1$ to $C_{10}$ alkoxy, cumene, mesitylene, toluene, and xylene;

provided that the tetracarboxylic acid compound is not 1,2,3,4-butane tetracarboxylic acid, and wherein the composition does not comprise a silicate, and wherein the composition does not comprise a phosphate.

2. The composition of claim 1, wherein $R_1$, $R_3$, $R_4$, and $R_5$ are each independently substituted with a $C_1$-$C_6$ alkylene group; and $R_2$ is CH or CHR', where R' is a $C_1$-$C_6$ alkylene group.

3. A corrosion inhibitor composition, comprising:
a tetracarboxylic acid compound selected from the group consisting of $C_3$-$C_{12}$ alkyl tetracarboxylic acid, $C_3$-$C_{12}$ aryl tetracarboxylic acid, $C_3$-$C_{12}$ cycloalkyl tetra carboxylic acid, aspartic acid N,N bis(carboxymethyl)-3-hydroxy, any salt thereof, and any combination thereof, and wherein the composition does not comprise a silicate, and wherein the composition does not comprise a phosphate.

4. The composition of claim 1, further comprising an additional corrosion inhibitor selected from the group consisting of zinc, tin, aluminum, manganese, nickel, molybdate, strontium, titanium, chromate, cobalt, cerium, any salt thereof, any oxide thereof, and any combination thereof.

5. The composition of claim 3, wherein the tetracarboxylic acid compound is selected from the group consisting of 1,2,3,4-butane tetracarboxylic acid, 1,1,2,3-propane tetracarboxylic acid, 1,2,4,5-benzene tetracarboxylic acid, 1,2,3,4-cyclopentane tetra carboxylic acid, any salt thereof, and any combination thereof.

6. The composition of claim 5, wherein the tetracarboxylic acid compound is 1,2,3,4-butane tetracarboxylic acid or any salt thereof and further comprising zinc or any salt thereof.

7. The composition of claim 5, wherein the tetracarboxylic acid compound is 1,2,3,4-butane tetracarboxylic acid or any salt thereof and further comprising molybdate or any salt thereof.

8. The composition of claim 5, wherein the tetracarboxylic acid compound is 1,2,3,4-butane tetracarboxylic acid or any salt thereof.

9. The composition of claim 5, wherein the tetracarboxylic acid compound is 1,2,3,4-butane tetracarboxylic acid or any salt thereof and further comprising tin or any salt thereof.

10. The composition of claim 1, further comprising a polymer comprising one or more monomers selected from the group consisting of acrylic acid, 2-acrylamido-2-methylpropane sulfonic acid, itaconic acid, tertiary butyl acrylamide, acrylamide, methacrylamide, and any combination thereof.

11. The composition of claim 10, further comprising an oligomeric maleic acid or oligomeric maleic anhydride of formula (II) or oligomeric maleic anhydride of formula (III)

(II)

(III)

where n is 1, 2, 3, 4, 5, or 6; and $R_6$ and $R_7$ are independently selected from the group consisting of hydrogen, $C_1$-$C_{10}$ alkyl, $C_4$ to $C_6$ aryl, $C_1$ to $C_{10}$ alkoxy, hydroxyl, cumene, mesitylene, toluene, and xylene.

12. The composition of claim 3, further comprising a byproduct or a reactant of a 1,2,3,4-butane tetracarboxylic acid chemical synthesis.

13. The composition of claim 1, wherein the composition comprises from about 5% to about 50% by weight of the tetracarboxylic acid compound.

14. The composition of claim 4, wherein the composition comprises from about 0.5% to about 15% by weight of the additional corrosion inhibitor.

15. The composition of claim 1, further comprising a triazole.

16. The composition of claim 1, wherein the composition excludes phosphorus or tetrazolium compounds.

17. A method of inhibiting corrosion of a metallic surface in an aqueous system comprising:
adding a corrosion inhibitor composition of claim 3 to the aqueous system, wherein the corrosion inhibitor composition comprises a tetracarboxylic acid compound and an additional corrosion inhibitor selected from the group consisting of zinc, tin, aluminum, manganese, nickel, silicate, molybdate, strontium, titanium, chromate, cobalt, cerium, any salt thereof, any oxide thereof, and any combination thereof.

18. The method of claim 17, wherein the tetracarboxylic acid compound is 1,2,3,4-butane tetracarboxylic acid or any salt thereof and the additional corrosion inhibitor is zinc or any salt thereof.

* * * * *

UNITED STATES PATENT AND TRADEMARK OFFICE
CERTIFICATE OF CORRECTION

PATENT NO. : 11,149,202 B1
APPLICATION NO. : 15/838936
DATED : October 19, 2021
INVENTOR(S) : Santanu Banerjee et al.

It is certified that error appears in the above-identified patent and that said Letters Patent is hereby corrected as shown below:

On the Title Page

Column 2, Line 10, item (56) OTHER PUBLICATIONS, "Pudovik, A.N.et al." should be --Pudovik, A.N. et al.--

Signed and Sealed this
Thirty-first Day of May, 2022

Katherine Kelly Vidal
*Director of the United States Patent and Trademark Office*